United States Patent
Jin et al.

(10) Patent No.: US 9,546,220 B2
(45) Date of Patent: Jan. 17, 2017

(54) COMPOSITIONS, ANTIBODIES, ASTHMA DIAGNOSIS METHODS, AND METHODS FOR PREPARING ANTIBODIES

(75) Inventors: Hongjun Jin, West Richland, WA (US); Richard C. Zangar, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 13/276,608

(22) Filed: Oct. 19, 2011

(65) Prior Publication Data
US 2012/0094860 A1    Apr. 19, 2012

Related U.S. Application Data

(60) Provisional application No. 61/394,640, filed on Oct. 19, 2010, provisional application No. 61/480,154, filed on Apr. 28, 2011.

(51) Int. Cl.
| | |
|---|---|
| A61K 39/395 | (2006.01) |
| C07K 16/00 | (2006.01) |
| C12P 21/08 | (2006.01) |
| C07K 16/44 | (2006.01) |
| G01N 33/68 | (2006.01) |

(52) U.S. Cl.
CPC ........... *C07K 16/44* (2013.01); *G01N 33/6812* (2013.01); *G01N 2800/122* (2013.01)

(58) Field of Classification Search
None
See application file for complete search history.

(56) References Cited

U.S. PATENT DOCUMENTS

| | | | |
|---|---|---|---|
| 6,306,576 B1 | 10/2001 | Hazen et al. | |
| 2002/0048775 A1* | 4/2002 | Hazen et al. | ............... 435/7.1 |
| 2002/0081624 A1 | 6/2002 | Billheimer et al. | |
| 2003/0180218 A1* | 9/2003 | Hazen | ............... 424/9.1 |
| 2005/0142626 A1 | 6/2005 | Hazen et al. | |
| 2006/0166295 A1 | 7/2006 | Woods et al. | |

FOREIGN PATENT DOCUMENTS

| | | |
|---|---|---|
| CN | 201180057478.2 | 5/2014 |
| JP | 2001500257 | 1/2001 |
| WO | WO 98/10294 | 3/1998 |
| WO | WO 2012/141737 | 10/2012 |
| WO | WO | 4/2013 |
| | PCT/US2011/056848 | |

OTHER PUBLICATIONS

PCT/US2011/056848 Search Report, Aug. 31, 2012, Battelle Memorial Institute.
PCT/US2011/056848 Written Opinion, Aug. 31, 2012, Battelle Memorial Institute.
Aldridge et al., "Eosinophil Peroxidase Produces Hypobromous Acid in the Airways of Stable Asthmatics", Free Radical Biology & Medicine, vol. 33, No. 6, 2002, pp. 847-856.
Wu et al., "3-Bromotyrosine and 3,5-Dibromotyrosine are Major Products of Protein Oxidation by Eosinophil Peroxidase: Potential Markers for Eosinophil-Dependent Tissue Injury in Vivo", Biochemistry 38, 1999, pp. 3538-3548.
Daly et al., "An Internal Calibration Method for Protein-Array Studies", Statistical Applications in Genetics and Molecular Biology vol. 9, Issue 1, Article 14 (2010) 23 pages.
Davis et al., "A Simple Modified Carbodiimide Method for Conjugation of Small-Molecular-Weight Compounds to Immunoglobulin G with Minimal Protein Crosslinking", Department of Microbiology and Cell Sciences, University of Florida Mar. 6, 1981, pp. 402-407.
Gonzalez et al., "Sandwich ELISA Microarrays: Generating Reliable and Reproducible Arrays for High-Throughput Screens", Methods in Pharmacology and Toxicology: Biomarker Methods in Drug Discovery and Development, Chapter 13, Humana Press, Totowa, NJ, Dec. 31, 2007, pp. 273-291.
Haurowitz et al., "The Specific Groups of Antibodies", The Institute of Biological and Medical Chemistry, University of Istanbul, Jan. 2, 1942, pp. 327-330.
Hawkins et al., "The Role of Reactive N-Bromo Species and Radical Intermediates in Hypobromus Acid-Induced Protein Oxidation", Free Radical Biology and Medicine 39 (2005) pp. 900-912.
Kambayashi et al., "Preparation and Characterization of a Polyclonal Antibody Against Brominated Protein", J. Clin. Biochem. Nutr., 44, (Jan. 2009) pp. 95-103.
Kato et al., "Immunogenicity of a Brominated Protein and Successive Establishment of a Monoclonal Antibody to Dihalogenated Tyrosine", Free Radical Biology and Medicine 38 (2005) pp. 24-31.

* cited by examiner

*Primary Examiner* — Nora Rooney
(74) *Attorney, Agent, or Firm* — Wells St. John P.S.

(57) ABSTRACT

Methods for preparing an antibody are provided with the method including incorporating 3-bromo-4-hydroxy-benzoic acid into a protein to form an antigen, immunizing a mammalian host with the antigen, and recovering an antibody having an affinity for the antigen from the host. Antibodies having a binding affinity for a monohalotyrosine are provided as well as composition comprising an antibody bound with monohalotyrosine. Compositions comprising a protein having a 3-bromo-4-hydroxy-benzoic acid moiety are also provided. Methods for evaluating the severity of asthma are provide with the methods including analyzing sputum of a patient using an antibody having a binding affinity for monohalotyrosine, and measuring the amount of antibody bound to protein. Methods for determining eosinophil activity in bodily fluid are also provided with the methods including exposing bodily fluid to an antibody having a binding affinity for monohalotyrosine, and measuring the amount of bound antibody to determine the eosinophil activity.

1 Claim, 5 Drawing Sheets

A. 3-Brominated KLH for immunization

B. NaOBr brominated BSA for screening of antibodies

COMPOSITIONS, ANTIBODIES, ASTHMA DIAGNOSIS METHODS, AND METHODS FOR PREPARING ANTIBODIES

CROSS REFERENCE TO RELATED APPLICATIONS

This application claims priority to U.S. Provisional Application Ser. No. 61/394,640 which was filed on Oct. 19, 2010, and U.S. Provisional Application Ser. No. 61/480,154 which was filed on Apr. 28, 2011, the entirety of each of which are incorporated by reference herein.

GOVERNMENT RIGHTS STATEMENT

This invention was made with Government support under Contract DE-AC0576RLO1830 awarded by the U.S. Department of Energy. The Government has certain rights in the invention. This research was also supported by the NIEHS Exposure Biology Program (U54/ES016015) and the US Department of Defense breast cancer postdoctoral fellowship W81XWH-10-1-0031.

TECHNICAL FIELD

The present disclosure relates to the preparation of antibodies and the use thereof. Particular embodiments of the disclosure related to the preparation of antibodies having an affinity for monohalotyrosine and proteins having monohalotyrosine moieties.

BACKGROUND

Asthma is a common disease that is characterized by an episodic narrowing of the airways. It is a major public health concern that affects about 23 million adults in the United States. Infiltration of activated eosinophils into the bronchioli is believed to be a primary cause of asthma. Eosinophil counts and the presence of secreted eosinophil granular proteins such as Eosinophil Peroxidase (EPO) in sputum and lung biopsy samples are indicators of the severity of asthma. Bromotyrosine protein modifications are increased in asthma patients due to EPO, which catalyzes the formation of hypobromite and the subsequent formation of bromotyrosine. Previous studies that used gas chromatography with mass spectrometric detection found that 3-bromotyrosine and 3,5-dibromotyrosine were significantly elevated in bronchoalveolar lavage fluid and sputum samples from asthmatics, respectively. Studies on the role of brominated proteins in asthma have been limited by the lack of a rapid, simple method to monitor bromotyrosine levels in biofluids.

SUMMARY OF THE DISCLOSURE

Additional advantages and novel features of the present disclosure will be set forth as follows and will be readily apparent from the descriptions and demonstrations set forth herein. Accordingly, the following descriptions of the present disclosure should be seen as illustrative of the disclosure and not as limiting in any way.

Bromotyrosine-modified proteins may be useful as stable biomarkers for airway oxidative stress. 3-bromotyrosine is believed to be the predominate bromotyrosine that occurs in vivo; however previous attempts have failed to produce a useful antibody that recognizes 3-bromotyrosine. For example, in 1930, Wormall reported producing rabbit antiserum against 3,5-dibromotyrosine, but failed in his attempt to generate a 3-bromotyrosine antibody. More recently, Kambayashi et al and Kato et al generated polyclonal and monoclonal antibodies against brominated proteins, but their antibodies also only react with 3,5-dibromotyrosine.

These failures to produce an antibody that recognizes 3-bromotyrosine may arise from the conditions used to produce the antigen. Mass spectrometry and nuclear magnetic resonance analyses indicate that dibromotyrosine modifications are preferentially produced relative to 3-bromotyrosine modifications as a result of in vitro protein bromination. It may be difficult to produce a good antigen for 3-bromotyrosine when using reagents that would be expected to mimic in vivo bromination.

The present disclosure describes provides antigen compositions that can include a protein having a 3-bromo-4-hydroxy-benzoic acid moiety. The present disclosure also provides methods for producing this antigen.

From this antigen an antibody having an affinity for halotyrosines can be identified that not only appears to recognize tyrosine residues that are monobrominated, but also binds other halogenated tyrosine residues. Methods for producing these antibodies having an affinity for this antigen as well as halotyrosines, including monohalotyrosines, are provided. Antibodies having an affinity for proteins having a halotyrosine moiety are provided as well as compositions that include the antibody bound the halotyrosine.

Furthermore, the disclosure demonstrates that the disclosed antibody is able to differentiate between levels of halotyrosine in human sputum proteins from healthy controls and asthmatics. Methods for evaluating the severity of asthma are provided as well as methods for determining eosinophil counts.

BRIEF DESCRIPTION OF THE DRAWINGS

Embodiments of the disclosure are described below with reference to the following accompanying drawings.

DESCRIPTION

Figure 1:
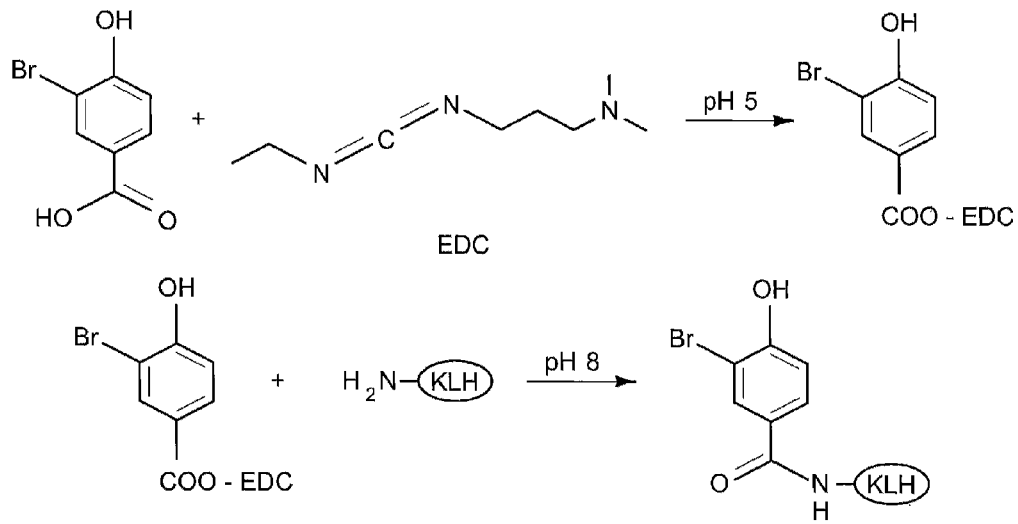
FIG. 1 are synthetic schemes for producing antigens according to an embodiment of the disclosure.
Figure 1:
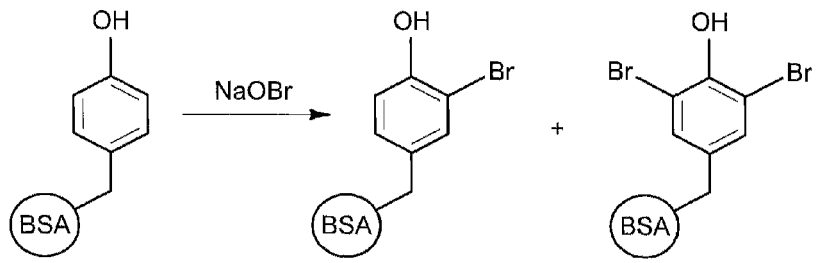

This disclosure is submitted in furtherance of the constitutional purposes of the U.S. Patent Laws "to promote the progress of science and useful arts" (Article 1, Section 8).

Various advantages and novel features of the present disclosure are described herein and will become further readily apparent to those skilled in this art from the following detailed description. In the preceding and following descriptions, embodiments of the disclosure are provided by way of illustration and description. As will be realized, the disclosure is capable of modification in various respects without departing from the disclosure. Accordingly, the drawings and description of the embodiments set forth hereafter are to be regarded as illustrative in nature, and not as restrictive.

The present disclosure provides compositions, antibodies, antigens, methods for producing antigens, methods for producing antibodies, and methods for evaluating asthma, as well as methods of determining eosinophil counts.

Methods for preparing an antibody are provided. The method can include incorporating a halo tyrosine analog such as 3-bromo-4-hydroxy-benzoic acid into a protein to form an antigen. The method can further include immunizing a mammalian host with the antigen, and recovering an antibody having an affinity for the antigen from the host. In accordance with example implementations the protein can be keyhole limpet hemocyanin (KLH). In accordance with this method a composition includes an antigen provided by modifying KLH with a compound that mimics 3-bromotyrosine. Accordingly a composition is provided that can include a protein having a 3-bromo-4-hydroxy-benzoic acid moiety, with the protein being KLH, for example.

In accordance with aspects of the disclosure, this can avoid the problem associated with in vitro protein bromination and the production primarily of dibromotyrosine. Bovine Serum Albumin (BSA) can then be brominated under conditions to optimize monobromination, and then used to screen hybridoma cell lines and to identify a clone that can have an affinity for physiologically relevant tyrosine modifications. This resulting BTK-94C antibody has an affinity for 3-bromotyrosine and 3,5-dibromotyrosine, also has an affinity for 3-chlorotyrosine and 3,5-dichlorotyrosine, but has no affinity for unmodified tyrosine, 3-nitrotyrosine or 3-hydroxytyrosine (see, e.g., FIGS. 2 and 4).

Chlorotyrosine modifications of proteins are also provided using hypochlorite, a product of myeloperoxidase, which is an enzyme found in neutrophil and macrophages. Because this antibody appears to bind all four physiologically relevant halogenated protein tyrosine residues, BTK-94C may be considered a general halotyrosine antibody.

Accordingly, methods of the disclosure provide an antibody having a binding affinity for protein halotyrosines and in particular embodiments, monohalotyrosine. The halotyrosine can be one or both of a monohalotyrosine and/or a dihalotyrosine. The monohalotyrosine can one or both of bromotyrosine and/or chlorotyrosine. The monohalotyrosine can also be one or both of 3-bromotyrosine and/or 3-chlorotyrosine. The dihalotyrosine can be one or both of 3,5-dibromotyrosine and/or 3,5-dichlorotyrosine. Compositions are also provided that include the antibody of the present disclosure bound to the antigen, with the antigen being the halotyrosine and/or halotyrosine protein.

Example implementations using antibodies of the present disclosure can overcome various problems associated with the previously used methods. Although there have been several polyclonal and monoclonal antibodies reported to react with brominated proteins, those antibodies appear to only react with dibromotyrosine, and not with 3-bromotyrosine. As 3-bromotyrosine is the predominate modification observed in vivo, this is an important limitation.

The present disclosure further provides methods that can include exposing the antibody to bodily fluid to determine one or more of eosinophil activity, inflammation, and/or an amount of protein having a monohalotyrosine and/or a dihalotyrosine moiety, for example.

Methods are also provided for evaluating the severity of asthma. The methods can include comprising analyzing sputum of a patient using an antibody having a binding affinity for monohalotyrosine, and measuring the amount of antibody bound to protein. The method can be one or both of qualitative and/or quantitative. The method can include correlating the amount of bound antibody to determine the amount of inflammation. The method may separately or together, include using the amount of bound antibody to monitor drug responses to asthma attacks.

Methods are also provided for determining eosinophil activity in bodily fluid. The methods can include exposing bodily fluid to an antibody having a binding affinity for monohalotyrosine, and measuring the amount of bound antibody to determine the eosinophil activity. The bodily fluid can be sputum or lavage fluid, for example. The method can also include correlating the amount of bound antibody to determine inflammation and/or drug responses, for example.

Accordingly, BTK-94C was tested with human sputum samples collected from asthmatics and healthy controls. An ELISA microarray analysis demonstrated that 4 proteins in human sputum samples are halogenated at increased levels in asthmatics. These data indicate that bromination is a specific indicator of eosinophil activity and that 4 specific proteins are modified in response to asthma-related eosinophil activity. Further, halogenation levels of these proteins may be useful in monitoring asthma.

Below is described a novel monoclonal antibody (BTK-94C) that recognizes brominated and chlorinated proteins. These halotyrosine protein modifications are indicative of inflammatory cell activity. This antibody was used as a detection reagent in sandwich ELISAs to demonstrate that halotyrosine levels of four sputum proteins are increased in asthmatics. Thus, the BTK-94C antibody can provide an indication of inflammation in asthmatics, and these ELISAs can prove useful for predicting or monitoring drug responses in asthma or in other diseases with a strong inflammatory component.

Example Materials and Methods

Bovine serum albumin (BSA) was purchased from Jackson ImmunoResearch Laboratory. 3-bromo-4-hydroxybenzoic acid was purchased from Indofine Chemical Company Inc. 3,5-dibromo-4-hydroxybenzalehyde, 3,5-dichloro-4-hydroxybenoic acid, 3,4-dihydroxybenic acid, 3-nitrotyrosine and L-tyrosine were purchased from Sigma-Aldrich. Keyhole limpet hemocyanin (KLH), 1-ethyl-3-(3-dimethylaminopropyl) carbodiimide (EDC), ascites conditioning reagent, Melon monoclonal antibody purification kit, and biotinylation kit EZ-link sulfo-NHS-biotin were purchased from Pierce-Thermo Scientific (Rockford, Ill.). Sodium hypobromite solution was purchased from Fisher-Thermo Scientific. Capture antibodies for 23 ELISA were purchased as stated in the supplementary data.

Example Preparation of the Brominated Antigen and Related Modified Proteins

For the preparation of the antigen, a modified protocol of the carbodiimide method as described in "*A Simple Modified Carbodiimide Method for Conjugation of Small-Molecular-Weight Compounds to Immunoglobulin G with Minimal Protein Crosslinking*", Minh-Tam B. Davis and James F. Preston, *Analytical Biochemistry* 116, 402-407 (1981), which is incorporated by reference herein, was used. Briefly, 0.12 mM 3-Br-HBA was dissolved in 2.5 ml methanol and combined with 0.75 mM EDC in 2.5 ml of 20 mM potassium phosphate buffer (pH 5.0) at room temperature for 2 min. This 5 ml solution was then mixed with 8 ml of 2.5 mg/ml KLH in 200 mM potassium phosphate buffer (pH 8.0) and allowed to incubate overnight at room temperature. Any remaining EDC and 3-Br-HBA were removed by dialysis against 120 mM PBS at 4° C. After dialysis, a precipitate was removed by centrifuge at 50,000 g for 2 h at 4° C. The modified antigen, in pH 8.0, 200 mM potassium phosphate buffer, was quantified by measuring the absorbance at 280 nm for protein concentration and 310 nm for bromination. The modified KLH was aliquotted and stored at −80° C.

Mice were immunized, serum collected, and hybridoma cell lines and their supernatants, ascites production, and antibody isotyping was undertaken at the Washington State University Monoclonal Antibody Center (Pullman). The BTK-94C antibody was biotinylated using the EZ-Link Sulfo-NHS-LC-Biotinylation Kit (Pierce, Rockford, Ill.), according to the manufacturer's protocol.

Brominated BSA was prepared using sodium hypobromite (Fisher Scientific, Pittsburgh, Pa.), as previously reported. To maximize the amount of 3-bromotyrosine relative to 3,5-dibromotyrosine, we used optimized conditions, as previously reported. That is, 1 ml of 10 mg BSA/ml was reacted with 200 µl of freshly prepared 20 mM sodium hypobromite (in pH 7.2 PBS) at 25° C. for 15 h. The solution was then dialyzed against PBS at 4° C. to remove unreacted reagents. To generate chlorinated BSA and nitrated BSA, 6% sodium hypochlorite (The Clorox Company) and peroxynitrite (Millipore Corporation, Boston, Mass.) were used, respectively, as previously reported.

Example, ELISA Microarray Assay and Inhibition Studies with Modified Tyrosine Analogs.

Sandwich ELISA microarray was performed as previously described except that the initial biotin signal was generated by goat-anti-mouse-IgM conjugated to horseradish peroxidase (Jackson ImmunoResearch Laboratories) in combination with biotinyltyramide. In brief, after centrifugation to remove any particulates, sputum samples were diluted 5-fold in 0.1% BSA in PBS. 25 µl of each diluted sample/chip was analyzed on three chips. Each chip contained 4 replicate spots for each capture antibody, such that there are a total of 12 replicates/sample for each of the 23 ELISAs. (See, e.g., Table 1 Below)

TABLE S1

Selected plasma biomarkers and references that relate these proteins to asthma.

| Capture antibodies | Abbreviation | Catalog # and Source |
|---|---|---|
| alpha-lactalbumin | a-LB | Sc-58672 [2] |
| amphiregulin | AmR | MAB262 [1] |
| ceruloplasmin | CP | sc-69767 [2] |
| C-reactive protein | CRP | MAB17071[1] |
| epidermal growth factor (EGF) | EGF | DY236 kit [1] |
| EGF receptor | EGFR | AF-231 [1] |
| E-selectin | Esel | AF-724 [1] |
| basic fibroblast growth factor | FGFb | MAB233 [1] |
| fibrinogen | Fibr | ID6-250310 [3] |
| heparin-binding epidermal growth factor | HBEGF | AF-292 [1] |
| hepatocyte growth factor | HGF | MAB694 [1] |
| intracellular adhesion molecular 1 | ICAM | MAB720 [1] |
| insulin-like growth factor 1 | IGF-1 | MAB291 [1] |
| leptin | Leptin | MAB398 [1] |
| matrix metalloprotease 1 | MMP1 | AF901 [1] |
| matrix metalloprotease 2 | MMP2 | AF902 [1] |
| matrix metalloprotease 9 | MMP9 | AF911 [1] |
| platelet-derived growth factor A | PDGF | MAB221 [1] |
| RANTES | RANTES | MAB678 [1] |
| surfactant protein A | SP-A | LS-C17957 [4] |
| transforming growth factor alpha | TGFa | AF-239 [1] |
| tumor necrosis factor alpha | TNFa | MAB610 [1] |
| vascular endothelial growth factor | VEGF | AF-293 [1] |

[1] R&D Systems; Minneapolis, MN, USA.
[2] Santa Cruz Biotechnology, Inc, Santa Cruz, CA USA.
[3] ABBiotek, San Diego CA, USA
[4] Lifespan Biosciences, Seattle WA, USA.

For the microarray assays to define antibody binding characteristics, modified and unmodified proteins were individually printed on aminopropylsilane-coated slides. The slides were then blocked with 2% BSA in PBS. 50 µL of the hybridoma supernatant was preincubated with 50 µL of a specific concentration of a chemical competitor (in 0.1% BSA/PBS) at room temperature for 12 h. Individual chemical competitors were serially diluted prior to mixing with the hybridoma supernatant. 25 µL of the mixture were loaded onto each microarray chip prior to incubation at room temperature for 16 h. The plate was washed three times with 0.05% Tween-20 in PBS, as previously described. The biotin signal was detected with streptavidin conjugated to Cy3, and then imaged using a ScanArray Express HT laser scanner (Perkin-Elmer, Downer Grove, Ill.). ScanArray Express software was used to analyze the images and determine the spot fluorescent signal.

Example ELISA Microarray

The printing and processing of the ELISA microarray chips has been previously described in detail in "*An Internal Calibration Method for Protein-Array Studies*", Don Simone Daly, et al, *Statistical Applications in Genetics and Molecular Biology*, Volume 9, Issue 1, 2010, Article 14, which is incorporated by reference herein. Green fluorescent protein (100 pg/mL) was spiked into each sputum sample and analyzed on the chip using a sandwich ELISA with separate capture and detection antibodies. Data from this analysis were used to normalize the data from the other ELISAs using ProMAT Calibrator, a custom bioinformatics program that we developed specifically for this purpose as described in "*An Internal Calibration Method for Protein-Array Studies*", Don Simone Daly, et al, *Statistical Applications in Genetics and Molecular Biology*, Volume 9, Issue 1, 2010, Article 14, and "*Preparation and Characterization of a Polyclonal Antibody Against Brominated Protein*", Yasuhiro Kambayashi, et al., *J. Clin. Biochem. Nutr.* 44, 95-103, January 2009, the entirety of each of which are incorporated by reference herein. ProMAT Calibrator is freely available at www.pnl.gov/statistics/ProMAT/. The procedures used for processing the microarray chips were essentially identical to those previously reported in "*An Internal Calibration Method for Protein-Array Studies*", Don Simone Daly, et al, *Statistical Applications in Genetics and Molecular Biology*, Volume 9, Issue 1, 2010, Article 14, except that only a single detection antibody was used.

In brief, each capture antibody was printed onto each chip in quadruplicate spots, once in each quadrant of the chip. In addition, antibodies for the GFP and orientation spots were printed in quadruplicate on each chip. Individual chips were incubated with one diluted sputum sample, and each sample was analyzed on three chips. The biotinylated halotyrosine monoclonal antibody that is described above (BTK-94C) was used to detect 3-bromotyrosine in the captured antigens. The processed slides were imaged with a ScanArray Express HT laser scanner (Perkin-Elmer, Downer Grove, Ill., USA) and ScanArray Express software was used to analyze the images and determine spot fluorescent intensity.

Example Statistics

Statistical comparisons were made using one-way analysis of variance {Chambers, 1992), when statistically significant, Tukey's Honest Significant Difference method was used to define which asthma groups had elevated levels of bromotyrosine. A probability value of $p<0.05$ was used to delineate statistical significance for all analyses.

Example Results
Evaluation of a Monoclonal Antibody for Halotyrosine.

Hypobromite reacts with protein tyrosines to produce both 3-bromotyrosine and 3,5-dibromotyrosine modifications (FIG. 1B). Procedures used for developing antigens containing either 3-brominated tyrosine or a related protein modification. A. Conjugation of 3-bromobenzoic acid to protein, as was used for generating the KLH antigen that was used for immunizing mice; B. Diagram of how sodium hypobromite is believed to modify tyrosine residues in vivo. This same chemistry was used to generate a modified BSA antigen that was used for screening hybridoma cell lines. Although the 3,5-dibromotyrosine modification predominates for the in vitro reaction, 3-bromotyrosine predominates in vivo. Thus, the fact that previous antibodies generated against in vitro brominated antigens only recognize the dibrominated tyrosine modifications suggests that this failure may reflect the antigen. For an antigen, a protein modification mimicking 3-bromotyrosine, namely a 3-bromo-4-hydroxy-benzonic-acid adducted to KLH was used. As such, it was confirmed that this artificial antigen produced antibodies that recognize a physiologically relevant brominated protein modification. Antibodies recovered from the serum from the mice immunized with the modified KLH antigen were found that did bind with brominated BSA, but not unmodified BSA (data not shown), indicating that the bromotyrosine mimic did result in antibodies that reacted with biologically relevant protein modifications.

The immunized mice were then used to generate 225 monoclonal hybridoma cell lines. Supernatants from these cultured cell lines were tested for reactivity and specificity using a custom protein microarray chip that contained individual spots of brominated BSA, chlorinated BSA, nitrated BSA, and unmodified BSA. These tests demonstrated that the BTK-94 antibody strongly reacted with brominated BSA, weakly reacted with chlorinated BSA, but did not react with unmodified BSA or nitrated BSA (FIG. 2).

Figure 2:
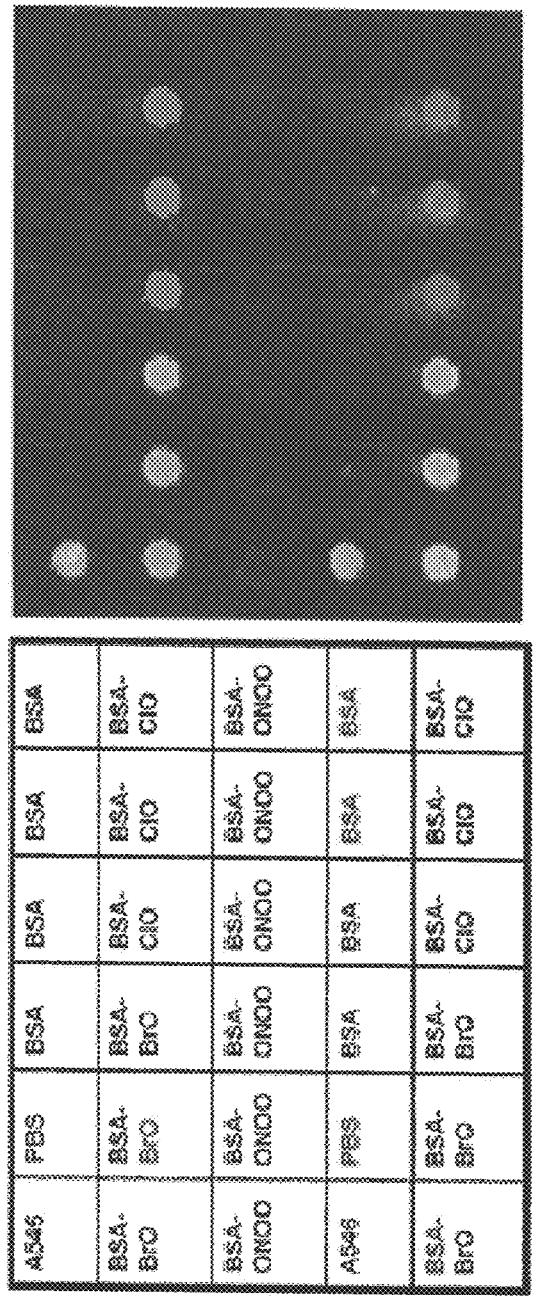
FIG. 2 is a depiction of an assay according of antibodies produced according to an embodiment of the disclosure.

FIG. 2 demonstrates the evaluation of recognition pattern of BTK-94C with different in vitro modified BSA. Left: pattern of antigens printed on the slide. Spot diameters are approximately 200 microns. Right: Cy3-scanned fluorescence image showing binding pattern of BTK-94C. A543, antibody modified with Alexa 543, which is used as an orientation spot; BSA-BrO, hypobromite-treated BSA; BSA-ClO hypochlorite-treated BSA; BSA-ONOO: peroxynitrite treated BSA.

This hybridoma cell line was further cultured to ensure that it was truly monoclonal. The BTK-94C antibody that is used in all subsequent tests was derived from these monoclonal cell lines. Tests indicated that this antibody had the same binding characteristics as shown for BTK-94 (FIG. 2).
Example Preparation and Characterization of Monoclonal Antibodies to Brominated Proteins.

Figure 3:
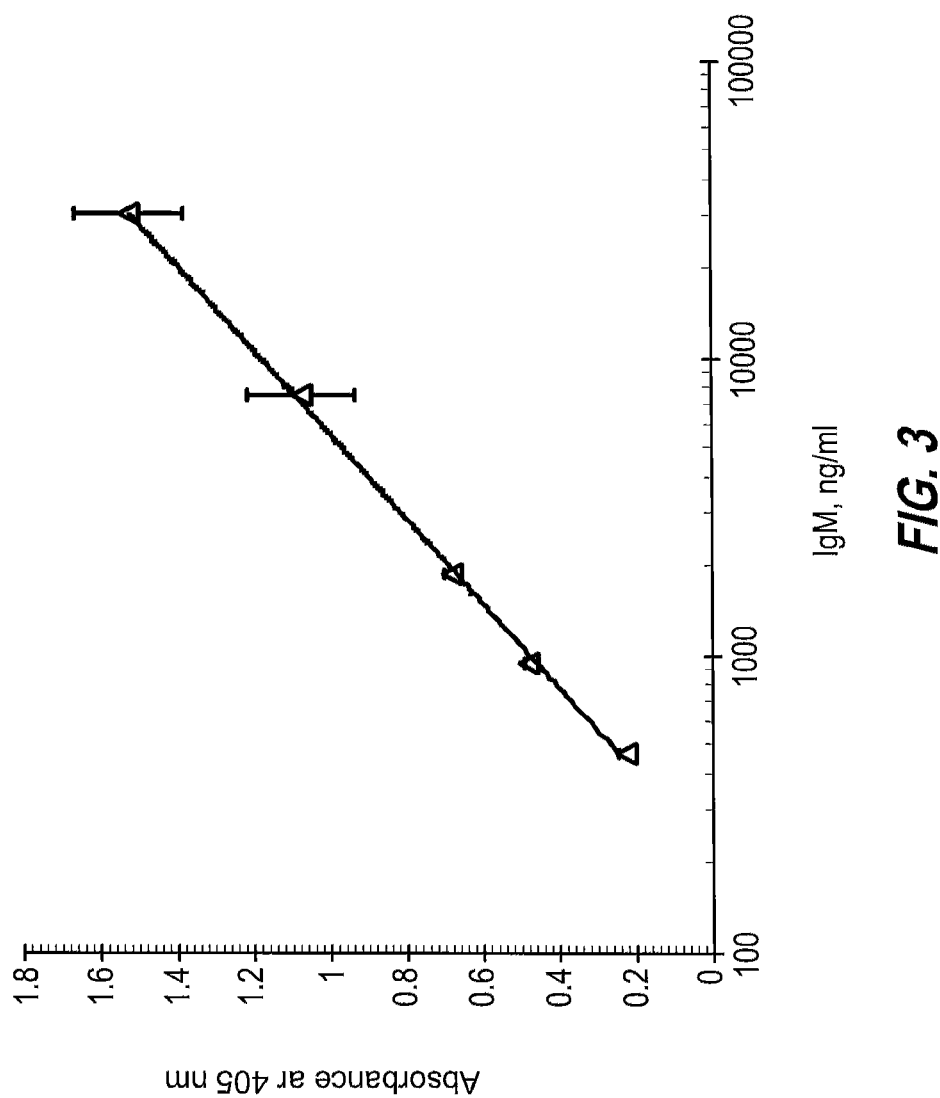
FIG. 3 is a depiction of data acquired utilizing antibodies produced according to an embodiment of the disclosure.

Isotyping of the BTK-94C indicated that this is an IgM antibody and reacted with brominated BSA in a concentration-dependent manner (FIG. 3). In FIG. 3, the signal produced with brominated BSA correlates with the concentration of the BTK-94C antibody. The ascites fluid from this cell line was also analyzed for specificity and cross-reactivity using protein microarray analysis. Consistent with results from hybridoma supernatants (see above), the BTK-94C antibody produced in the ascites bound brominated and chlorinated BSA, but no reactivity with unmodified or peroxynitrite-treated BSA was observed (data not shown), further confirming that this antibody preferentially reacts with halogenated proteins.

Figure 4:
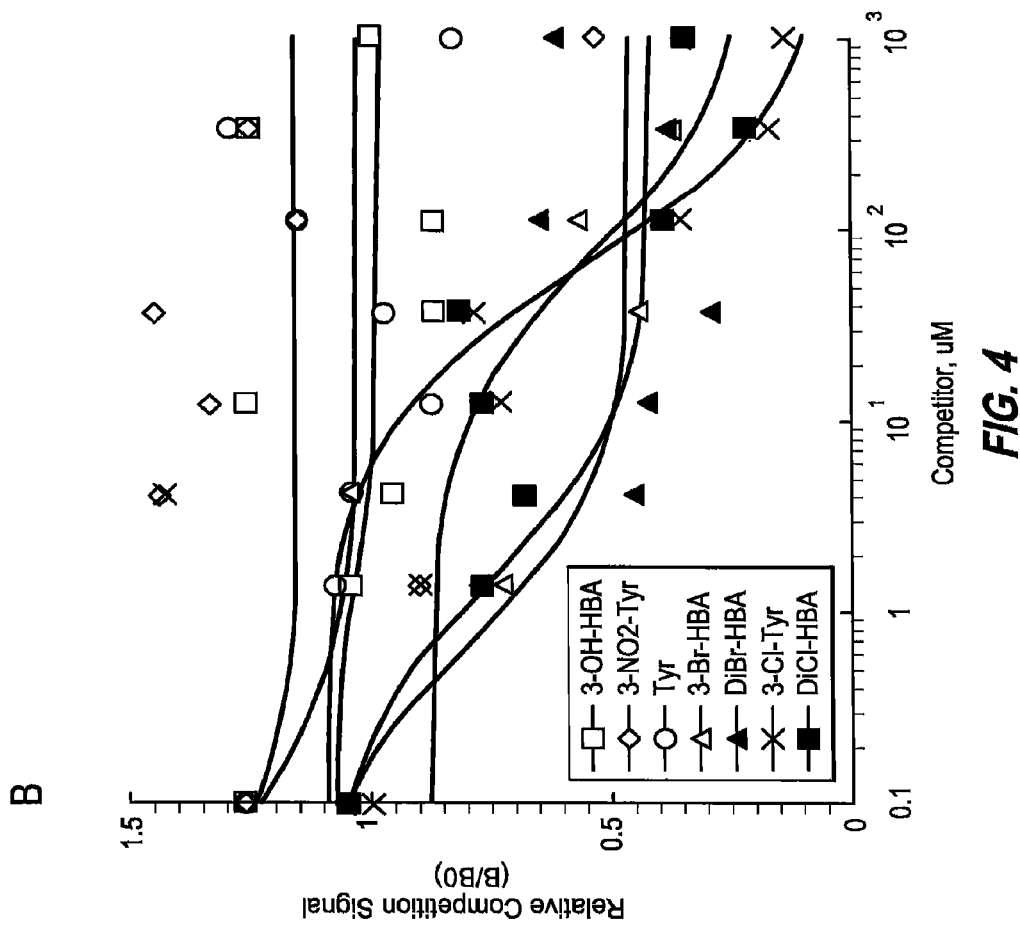
FIG. 4 is a depiction moieties of proteins, and data acquired utilizing antibodies produced according to an embodiment of the disclosure.

To further characterize the specificity of this antibody, the ability of reagents that mimic tyrosine modifications to inhibit the BTK-94C antibody binding to brominated BSA was evaluated. The binding of BTK-94C to brominated BSA was strongly inhibited by 3-bromo-4-hydroxybenzoic acid and 3,5-dibromo,4-hydroxybenzoic acid, but less potently inhibited by 3-chlorotyrosine and 3,5-dichloro,4-hydroxybenzoic acid (FIG. 4B). Binding to brominated BSA was not inhibited by intact tyrosine, 3-nitrotyrosine or 3,4-dihydroxybenzoic acid (FIG. 4).

Referring to FIG. 4, binding properties of BTK-94C to brominated albumin based on inhibition by modified tyrosine analogs is shown. The individual chemicals and BTK-94C were incubated overnight and then added to protein microarray chips printed with brominated BSA. Abbreviations and related chemical names and structures are shown in panel A: 3-Br-HBA, 3-bromo-4-hydroxybenzoic acid; DiBr-HBA, 3,5-dibromo-4-hydroxybenzalehyde, DiCl-HBA, 3,5-dichloro-4-hydroxybenoic acid, 3-OH-HBA3,4-dihydroxybenic acid, 3-NO2-Tyr, 3-nitrotyrosine and Tyr, L-tyrosine. Panel B: The results were expressed as relative competition as B/B0, where B is the amount of antibody bound in the presence of competitor and B0 is the amount in the absence of the competitor. Each point represents the median of triplicate analyses. These results further suggest that BTK-94C recognizes 3-bromotyrosine as well as chlorotyrosine protein modifications.
Example BTK-94C Analysis of Halogenated Tyrosine Modifications in Human Sputum Proteins.

To determine if this antibody has potential for evaluating eosinophil activity in asthmatics, an ELISA microarray platform was utilized that employed BTK-94C as the sole detection antibody. On this ELISA chip, were printed 23 capture antibodies for antigens that are potentially related to asthma (see supplementary data). Of these captured antigens, a statistically significant increase in the bromination levels of AGT, ICAM, PDGF and RANTES in asthmatics with either high eosinophil or low eosinophils counts in the sputum samples when compared to the healthy controls was observed. (FIG. 5).

Figure 5:
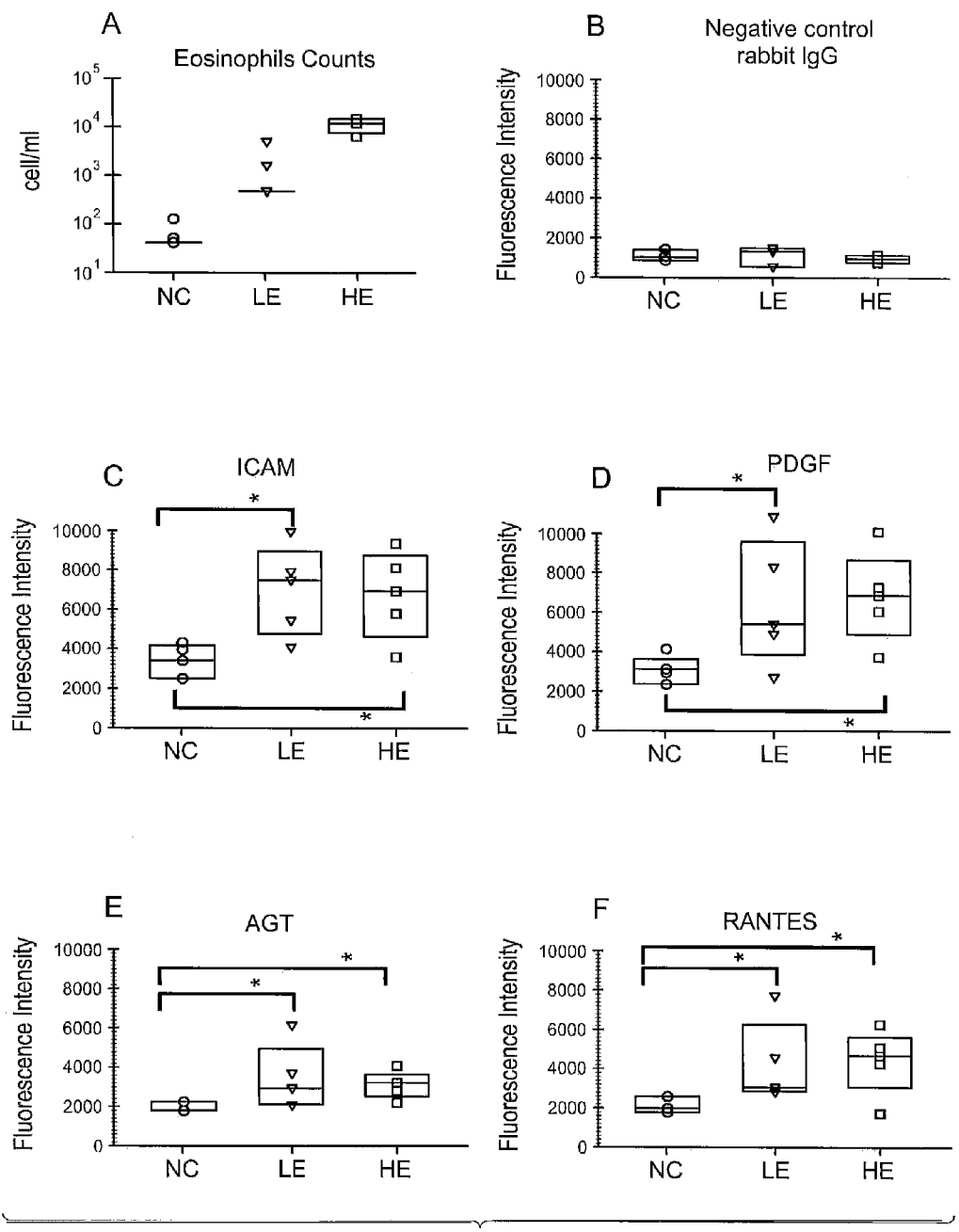
FIG. 5 is a depiction of data acquired utilizing antibodies produced according to an embodiment of the disclosure

Referring to FIG. 5, halogenated proteins are elevated in protein present in sputum from asthmatics. (A). Eosinophils counts from sputum samples tested in this study. (B) Non-immune rabbit IgG was printed onto the ELISA microarray as a negative control spot showed completely flat signal through all tested sputum samples. Halotyrosine levels for intracellular adhesion molecular 1 (ICAM) (C), platelet-derived growth factor AA (PDGF) (D), AGT (E), and RANTES (F). The lateral line represents the median values, and boxes are the $25^{th}$ and 75 quantile's.

Data from ELISA microarray analysis indicates significantly different ($p<0.05$) based on ANOVA and Turkey's test. In contrast, the other 19 assays that were performed with this chip did not show any significant differences. For the ELISA microarray analysis, nonimmune rabbit IgG was printed as a negative control. The signal from this spot was low in comparison to others, and there were no treatment-related changes in this signal (FIG. 5B), suggesting that the differential signal associated with asthma that was observed in the spots containing capture antibodies was due to differential halogenation of the captured antigens.

In compliance with the statute, embodiments of the disclosure have been described in language more or less specific as to structural and methodical features. It is to be understood, however, that the entire disclosure is not limited to the specific features and/or embodiments shown and/or described, since the disclosed embodiments comprise forms of putting the disclosure into effect. The disclosure is, therefore, claimed in any of its forms or modifications within the proper scope of the appended claims appropriately interpreted in accordance with the doctrine of equivalents.

The invention claimed is:

1. A general halotyrosine antibody consisting of BTK-94C antibody, having accession number PTA-123084.

* * * * *

UNITED STATES PATENT AND TRADEMARK OFFICE
CERTIFICATE OF CORRECTION

PATENT NO. : 9,546,220 B2
APPLICATION NO. : 13/276608
DATED : January 17, 2017
INVENTOR(S) : Hongjun Jin and Richard C. Zangar It is certified that error appears in the above-identified patent and that said Letters Patent is hereby corrected as shown below:

In the Specification

Column 1, Line 28 – Replace "disclosure related" with --disclosure are related--

Column 2, Line 14 – Replace "disclosure describes provides" with --disclosure provides--

Column 2, Line 26 – Replace "bound the" with --bound to the--

Column 2, Line 40 – Replace "according of antibodies" with --according to antibodies--

Column 2, Line 44 – Replace "depiction moieties" with --depiction of moieties--

Column 3, Line 39 – Replace "can one or both" with --can be one or both--

Column 3, Line 61 – Replace "can include comprising analyzing" with --can include analyzing--

Column 6, Line 63 – Replace "{Chambers, 1992)" with --(Chambers, 1992)--

Column 7, Line 20 – Replace "mimicing" with --mimicking--

Column 8, Line 19 – Replace "hydroxybenoic acid" with --hydroxybenzoic acid--

Signed and Sealed this
Twenty-seventh Day of June, 2017

Joseph Matal
*Performing the Functions and Duties of the*
*Under Secretary of Commerce for Intellectual Property and*
*Director of the United States Patent and Trademark Office*